United States Patent
Banik et al.

[11] Patent Number: 5,871,453
[45] Date of Patent: Feb. 16, 1999

[54] MOVEABLE SAMPLE TUBE MULTIPLE BIOPSY SAMPLING DEVICE

[75] Inventors: Michael S. Banik, Cincinnati; Joseph E. Young, Loveland; Scott E. Swaffar, Cincinnati; Michael B. Mosholder, Powell; Kenneth E. Hughes, Gahanna; Jan B. Yates, Reynoldsburg; Norman J. Hedman, Hilliard; Jeremy M. Harris, Worthington; Alan A. Alten, Baltimore, all of Ohio

[73] Assignee: Boston Scientific Corporation, Watertown, Mass.

[21] Appl. No.: 705,922

[22] Filed: Aug. 29, 1996

Related U.S. Application Data

[63] Continuation of Ser. No. 193,382, Feb. 8, 1994, abandoned.

[51] Int. Cl.[6] ....................................................... A61B 5/00
[52] U.S. Cl. ............................................................. 600/564
[58] Field of Search ..................... 128/749, 751, 128/753, 754; 606/167–172, 177, 178, 186, 205, 207; 600/564–567

[56] References Cited

U.S. PATENT DOCUMENTS

| | | |
|---|---|---|
| 612,569 | 10/1898 | Moscrop . |
| 668,647 | 2/1901 | Jaenicke . |
| 1,162,901 | 12/1915 | Cantey . |
| 1,606,497 | 11/1926 | Berger . |
| 1,867,624 | 7/1932 | Hoffman . |
| 1,891,054 | 12/1932 | Pitman . |
| 2,426,535 | 8/1947 | Turkel . |
| 2,493,979 | 1/1950 | Kudd . |
| 2,541,542 | 2/1951 | Perez et al. . |
| 2,749,909 | 6/1956 | Ullery et al. ................................ 128/2 |
| 2,850,007 | 9/1958 | Lingley ....................................... 128/2 |
| 3,001,522 | 9/1961 | Silverman . |
| 3,147,749 | 9/1964 | Marsh ....................................... 128/751 |
| 3,175,554 | 3/1965 | Stewart . |
| 3,181,533 | 5/1965 | Heath . |
| 3,342,175 | 9/1967 | Bulloch . |
| 3,477,423 | 11/1969 | Griffith ...................................... 128/2 |
| 3,590,808 | 7/1971 | Muller ....................................... 128/2 |

(List continued on next page.)

FOREIGN PATENT DOCUMENTS

| | | |
|---|---|---|
| 0 279 358 | 8/1988 | European Pat. Off. . |
| 2 479 680 | 10/1981 | France . |
| 1215439 | 12/1970 | United Kingdom . |
| 91/02493 | 3/1991 | WIPO . |
| 92/11882 | 7/1992 | WIPO . |
| WO 93/04630 | 3/1993 | WIPO . |
| WO 94/15533 | 7/1994 | WIPO . |

OTHER PUBLICATIONS

Radial Jaw Single–Use Biopsy Forceps, Boston Scientific Corporation, 1993.

Grossman, "Gastrointestinal Endoscopy", Clinical Symposia, vol. 32, No. 3, 1980.

For the ultimate experience in multiple endoscopic biopsies, Triton, Date Unknown.

*Primary Examiner*—Max Hindenburg
*Attorney, Agent, or Firm*—Finnegan, Henderson, Farabow, Garrett, & Dunner, L.L.P.

[57] ABSTRACT

An instrument for obtaining tissue samples from a site deep within the body. The instrument has an elongated proximal portion that is constructed to follow a long, torturous path to the site and has a distal end constructed to sever and remove a tissue sample from the body, including tissue specimens, polyps or the like. The instrument is constructed to take multiple biopsy samples without being withdrawn from the body. The instrument includes a tissue sample retractor. The retractor is axially movable between an extended tissue-engaging position and a retracted position. There is an open passage into which the retractor moves when moving from the extended to the retracted position. The retractor has a distal end portion constructed to engage tissue and apply axial transporting force thereto while moving from the extended to the retracted position. The retractor is constructed to be advanced and retracted repeatedly to accumulate a series of samples in the instrument.

39 Claims, 12 Drawing Sheets

U.S. PATENT DOCUMENTS

| | | | |
|---|---|---|---|
| 3,606,878 | 9/1971 | Kellogg, Jr. | 128/2 |
| 3,683,892 | 8/1972 | Harris | 128/2 |
| 3,692,020 | 9/1972 | Schied | 128/2 |
| 3,732,858 | 5/1973 | Banko | 128/2 |
| 3,882,849 | 5/1975 | Jamshidi | 128/2 |
| 3,903,892 | 9/1975 | Komiya | 128/303 |
| 3,924,608 | 12/1975 | Mitsui | 128/751 X |
| 3,955,578 | 5/1976 | Chamness et al. | |
| 3,989,033 | 11/1976 | Halpern et al. | |
| 3,989,049 | 11/1976 | Yoon | |
| 3,996,935 | 12/1976 | Banko | |
| 4,007,732 | 2/1977 | Kvavle et al. | |
| 4,020,847 | 5/1977 | Clark, III | |
| 4,168,698 | 9/1979 | Ostergard | |
| 4,174,715 | 11/1979 | Hasson | |
| 4,178,810 | 12/1979 | Takahashi | |
| 4,200,111 | 4/1980 | Harris | |
| 4,220,155 | 9/1980 | Kimberling et al. | |
| 4,243,048 | 1/1981 | Griffin | |
| 4,282,884 | 8/1981 | Boebel | |
| 4,326,530 | 4/1982 | Fleury, Jr. | |
| 4,393,872 | 7/1983 | Reznik et al. | 604/151 |
| 4,427,014 | 1/1984 | Bel et al. | |
| 4,461,305 | 7/1984 | Cibley | |
| 4,493,320 | 1/1985 | Treat | 128/303 |
| 4,509,517 | 4/1985 | Zibelin | |
| 4,522,206 | 6/1985 | Whipple et al. | 128/312 |
| 4,574,803 | 3/1986 | Storz | 128/305 |
| 4,620,547 | 11/1986 | Boebel | 128/754 |
| 4,651,752 | 3/1987 | Fuerst | |
| 4,651,753 | 3/1987 | Lifton | 128/751 |
| 4,662,371 | 5/1987 | Whipple et al. | 128/312 |
| 4,682,606 | 7/1987 | DeCaprio | |
| 4,693,257 | 9/1987 | Markham | 128/752 |
| 4,708,147 | 11/1987 | Haaga | |
| 4,712,550 | 12/1987 | Sinnett | |
| 4,721,116 | 1/1988 | Schintgen et al. | 128/751 |
| 4,733,662 | 3/1988 | DeSatnick et al. | 128/305 |
| 4,735,215 | 4/1988 | Goto et al. | 128/754 |
| 4,763,668 | 8/1988 | Macek et al. | 128/751 |
| 4,785,826 | 11/1988 | Ward | |
| 4,817,630 | 4/1989 | Schintgen et al. | 128/751 |
| 4,830,002 | 5/1989 | Semm | 128/321 |
| 4,867,156 | 9/1989 | Stack et al. | 128/305 |
| 4,881,550 | 11/1989 | Kothe | 128/752 |
| 4,887,612 | 12/1989 | Esser et al. | 128/751 |
| 4,903,709 | 2/1990 | Skimmer | 128/754 |
| 4,909,782 | 3/1990 | Semm et al. | 606/171 |
| 4,926,877 | 5/1990 | Bookwalter | 128/754 |
| 4,936,845 | 6/1990 | Stevens | |
| 4,953,559 | 9/1990 | Salerno | 128/751 |
| 4,971,067 | 11/1990 | Bolduc et al. | 128/751 |
| 4,976,269 | 12/1990 | Mehl | 128/754 |
| 4,986,825 | 1/1991 | Bays et al. | 604/22 |
| 5,026,379 | 6/1991 | Yoon | 606/141 |
| 5,052,402 | 10/1991 | Bencini et al. | 128/751 |
| 5,074,311 | 12/1991 | Hasson | 128/754 |
| 5,082,000 | 1/1992 | Picha et al. | 128/751 |
| 5,085,658 | 2/1992 | Meyer | 606/46 |
| 5,085,659 | 2/1992 | Rydell | |
| 5,098,440 | 3/1992 | Hillstead | 606/108 |
| 5,111,828 | 5/1992 | Kornberg et al. | 128/754 |
| 5,133,360 | 7/1992 | Spears | |
| 5,133,727 | 7/1992 | Bales et al. | 606/170 |
| 5,147,378 | 9/1992 | Markham | 606/206 |
| 5,148,813 | 9/1992 | Bucalo | 128/754 |
| 5,171,255 | 12/1992 | Rydell | |
| 5,172,700 | 12/1992 | Bencini et al. | 128/751 |
| 5,195,533 | 3/1993 | Chin et al. | 128/754 |
| 5,197,484 | 3/1993 | Kornberg et al. | 128/754 |
| 5,211,655 | 5/1993 | Hasson | 606/205 |
| 5,217,458 | 6/1993 | Parins | 606/48 |
| 5,217,468 | 6/1993 | Clement | 606/127 |
| 5,224,488 | 7/1993 | Neuffer | 128/751 |
| 5,228,451 | 7/1993 | Bales et al. | 128/751 |
| 5,234,000 | 8/1993 | Hakky et al. | 128/754 |
| 5,238,002 | 8/1993 | Devlin et al. | 128/751 |
| 5,242,461 | 9/1993 | Kortenbach et al. | |
| 5,251,641 | 10/1993 | Xavier | 128/754 |
| 5,267,572 | 12/1993 | Bucalo | 128/754 |
| 5,281,230 | 1/1994 | Heidmueller | 606/127 |
| 5,292,310 | 3/1994 | Yoon | |
| 5,318,589 | 6/1994 | Lichtman | 600/564 |
| 5,331,971 | 7/1994 | Bales et al. | 128/749 X |
| 5,334,198 | 8/1994 | Hart et al. | 606/52 |
| 5,342,390 | 8/1994 | Slater et al. | 128/749 X |
| 5,373,854 | 12/1994 | Kolozsi | |
| 5,375,608 | 12/1994 | Tiefenbrun et al. | |
| 5,383,471 | 1/1995 | Funnell | 128/751 |
| 5,394,887 | 3/1995 | Haaga | 128/754 |
| 5,542,432 | 8/1996 | Slater et al. | 606/751 |
| 5,573,008 | 11/1996 | Robinson et al. | 128/754 |

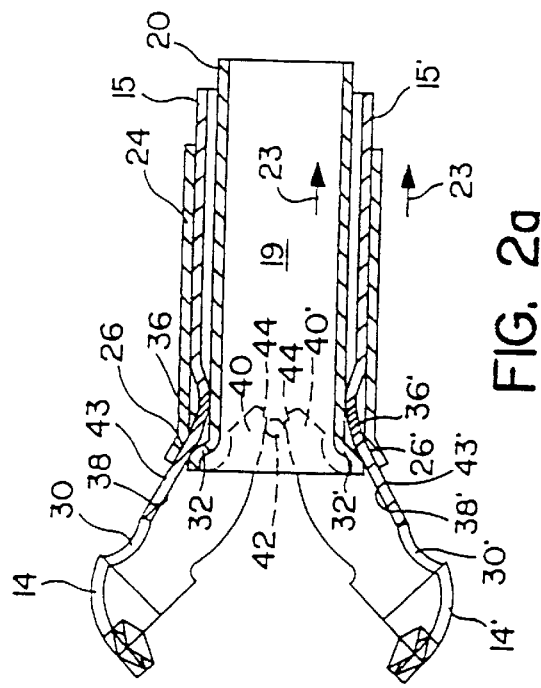
FIG. 2a
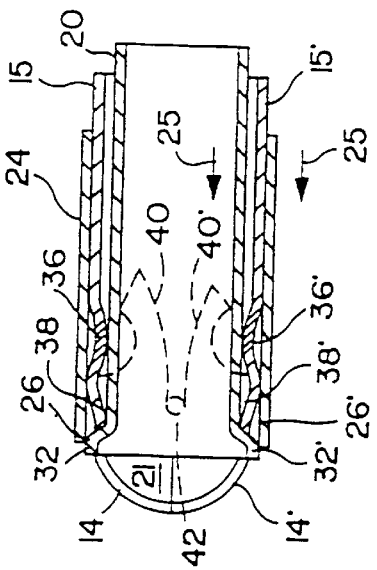
FIG. 3a
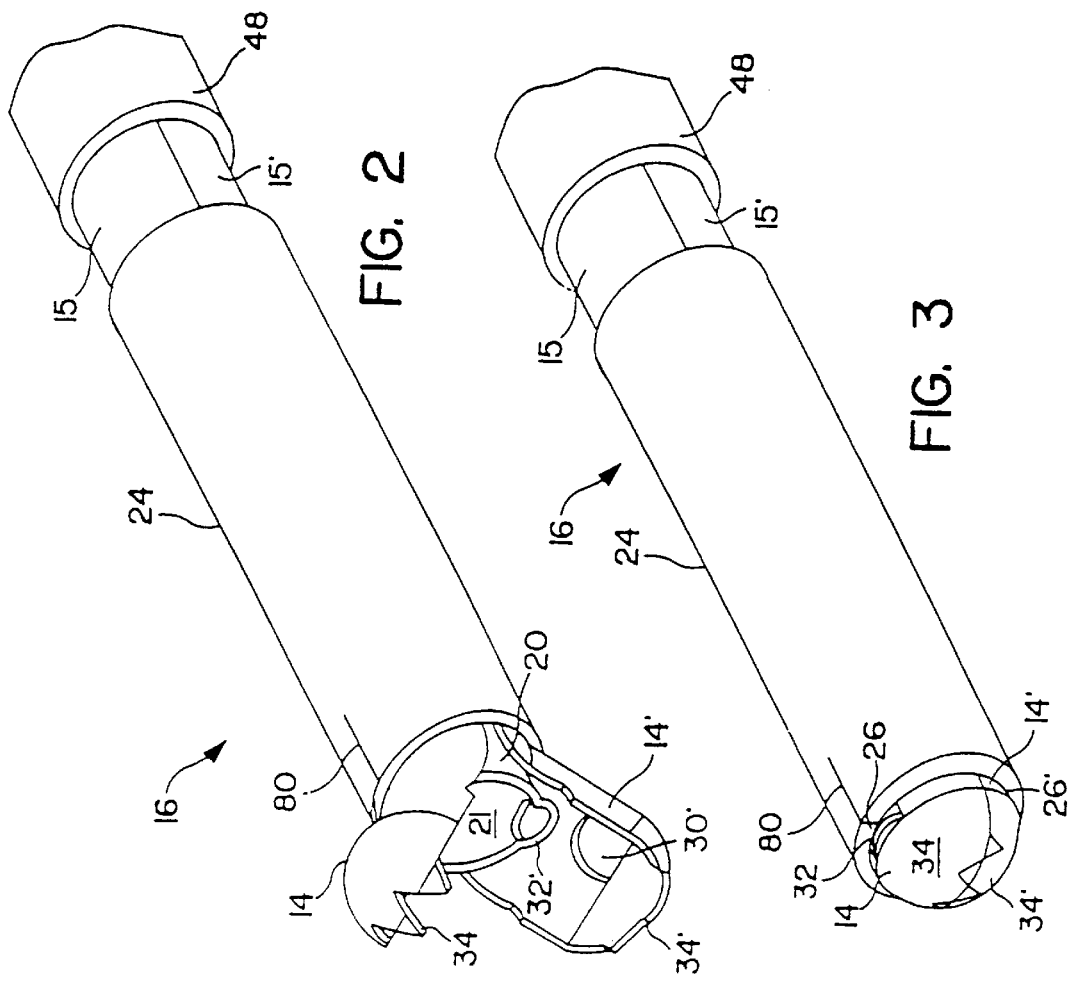
FIG. 2
FIG. 3

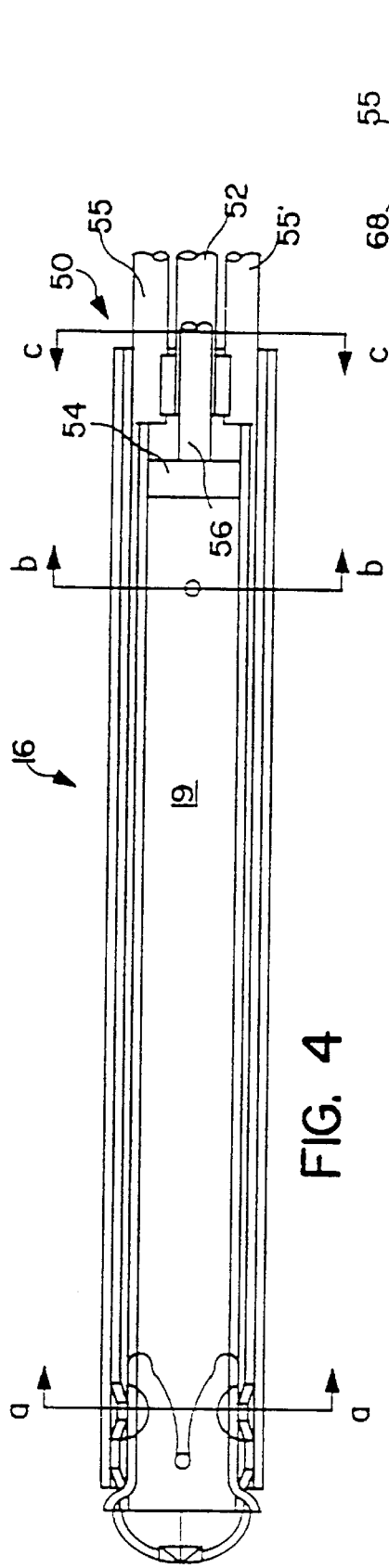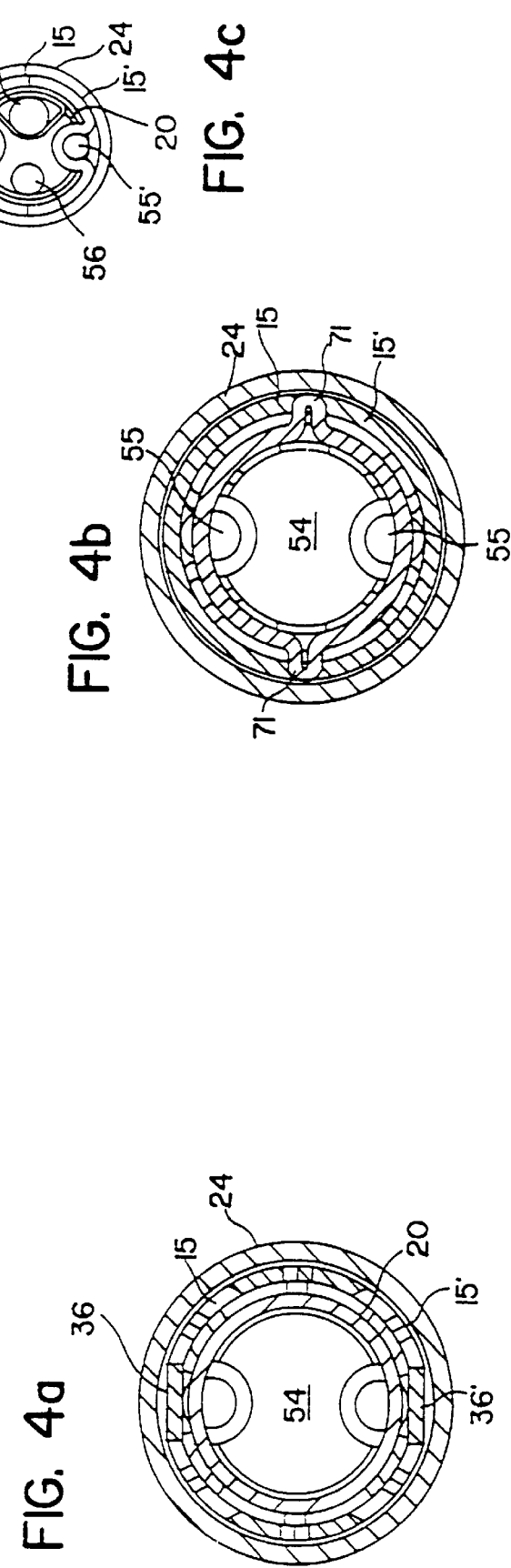

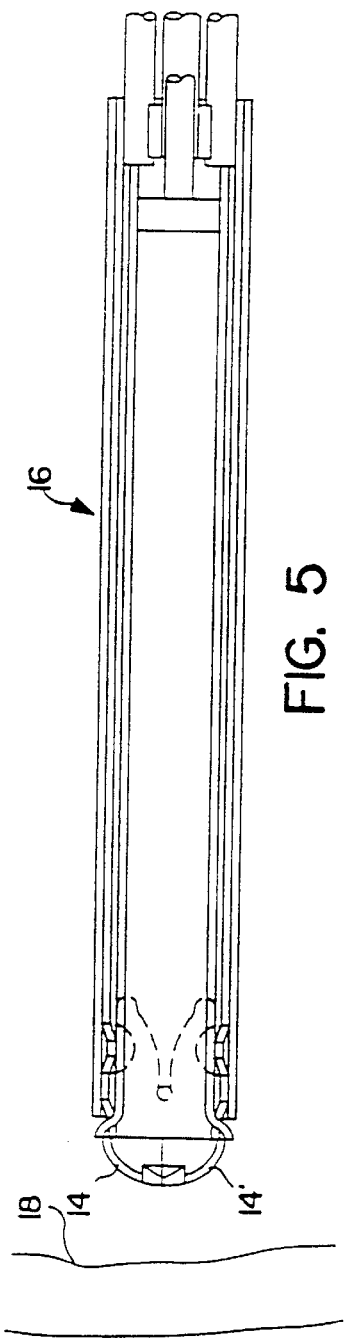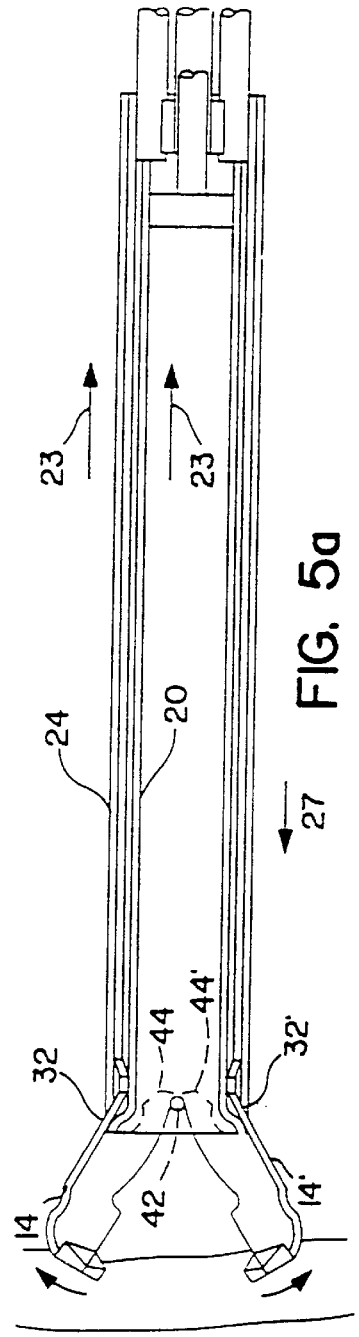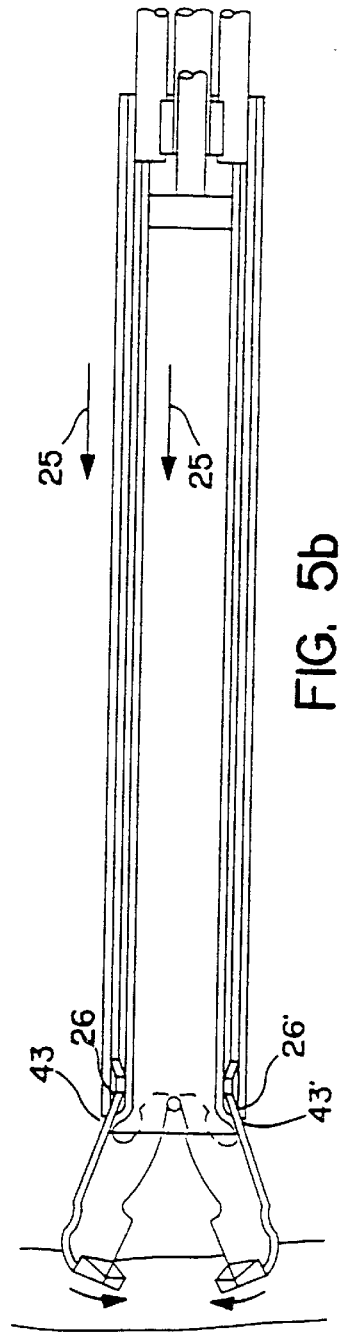

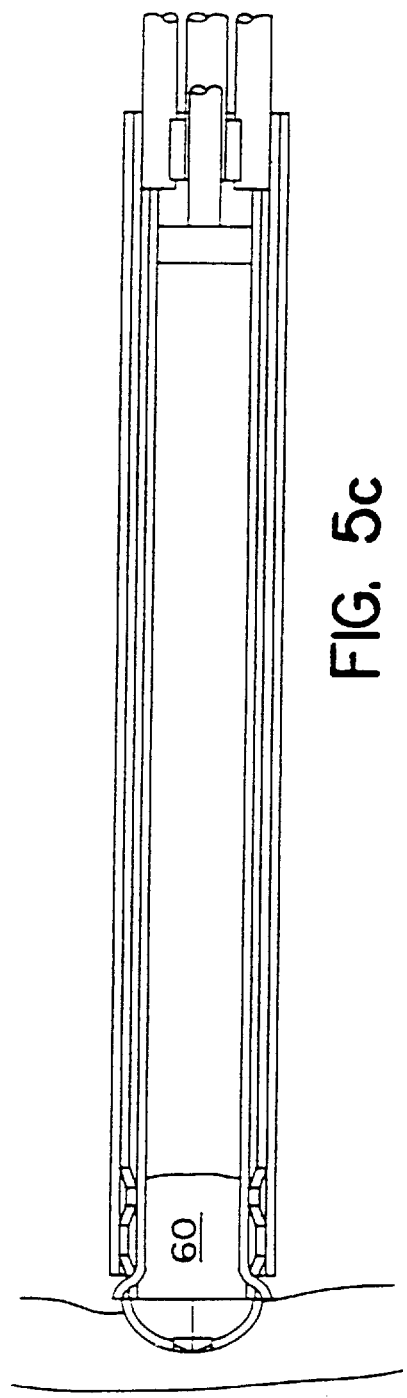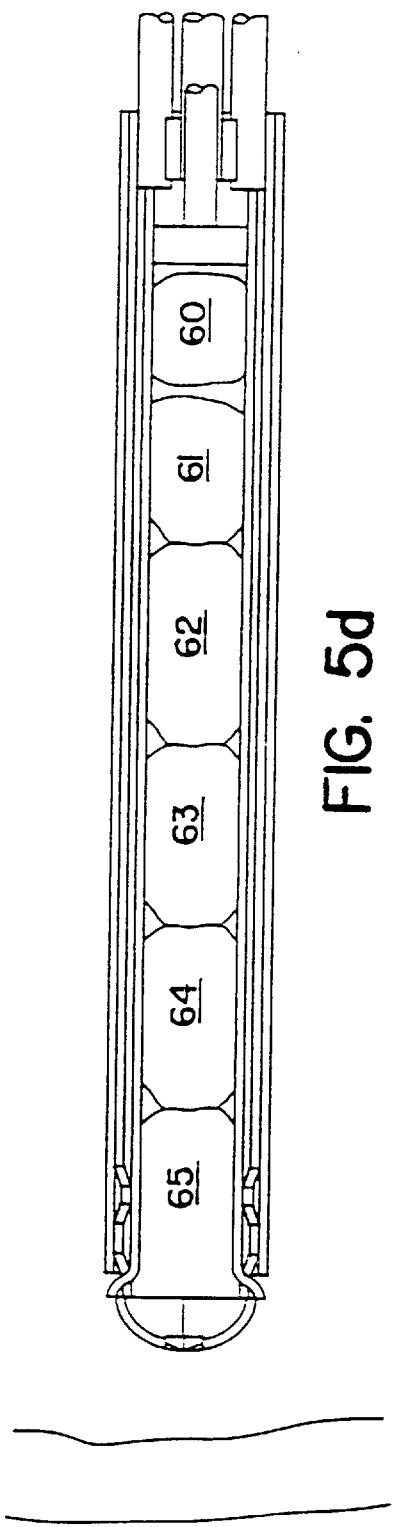

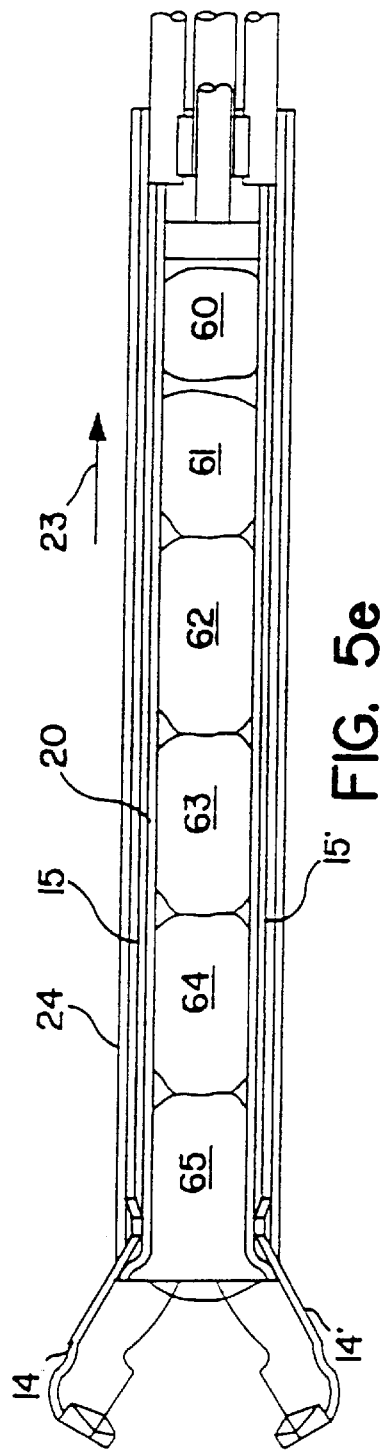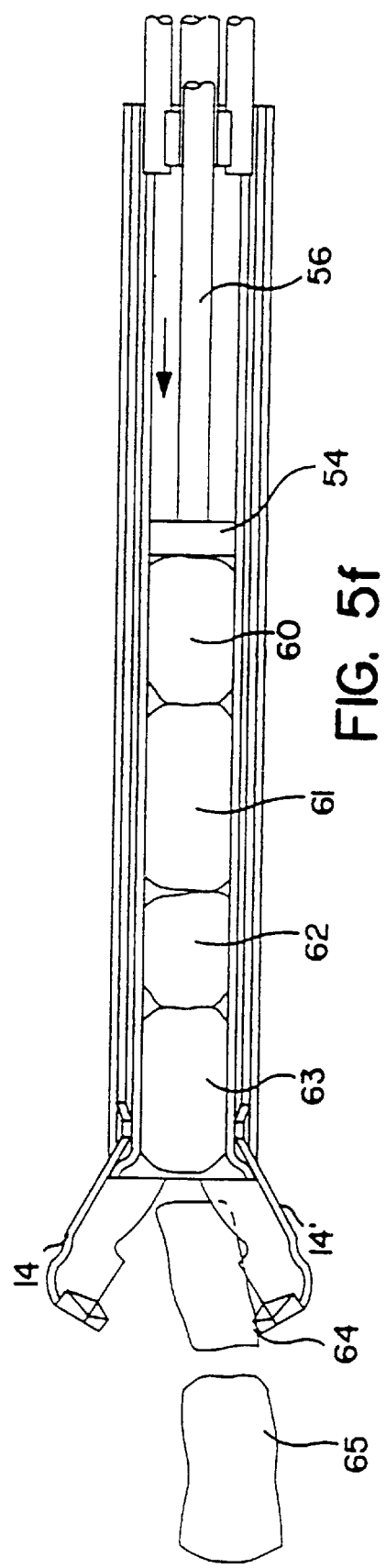

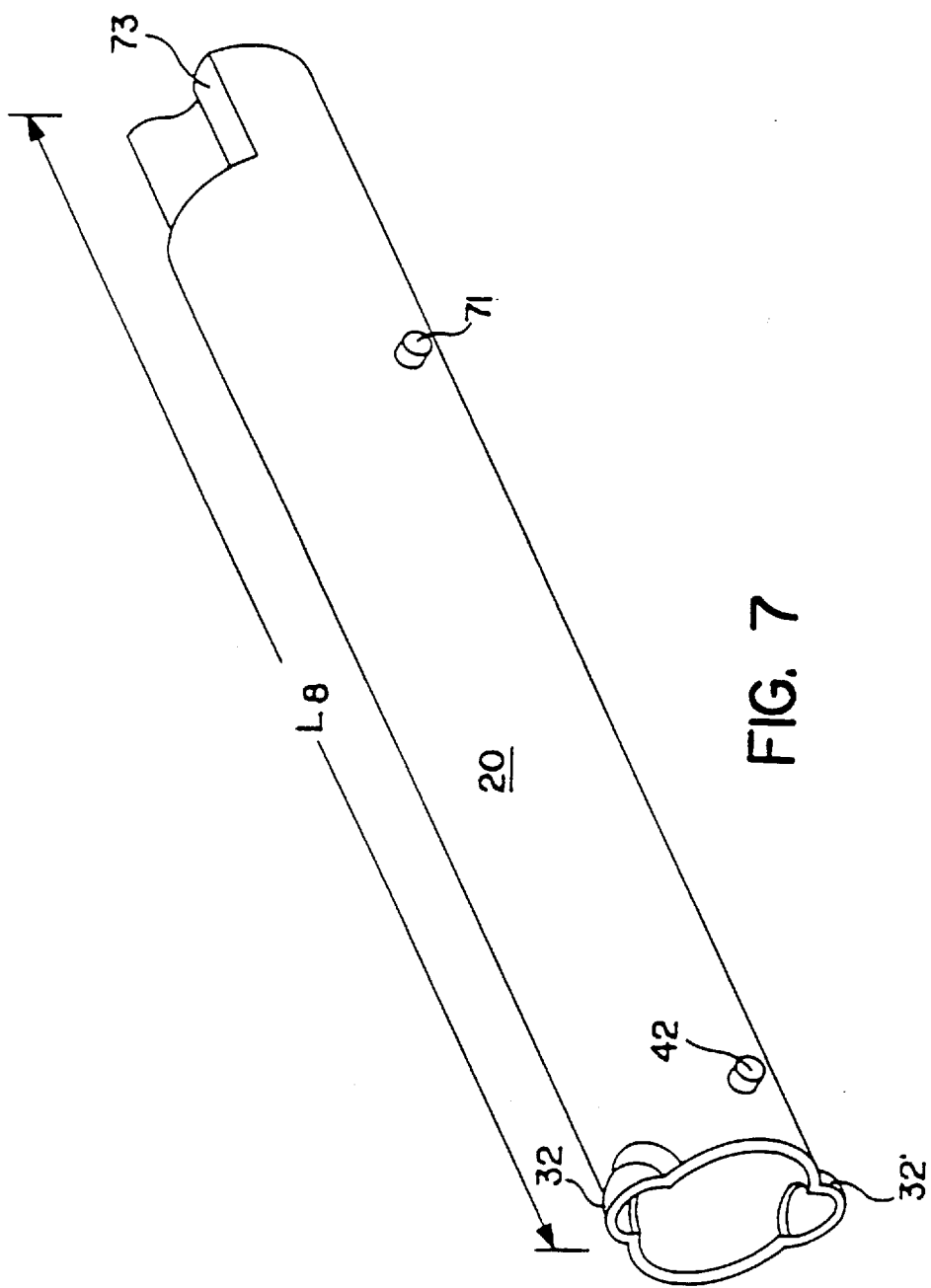

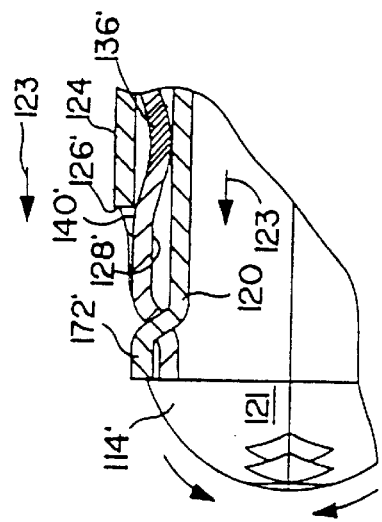
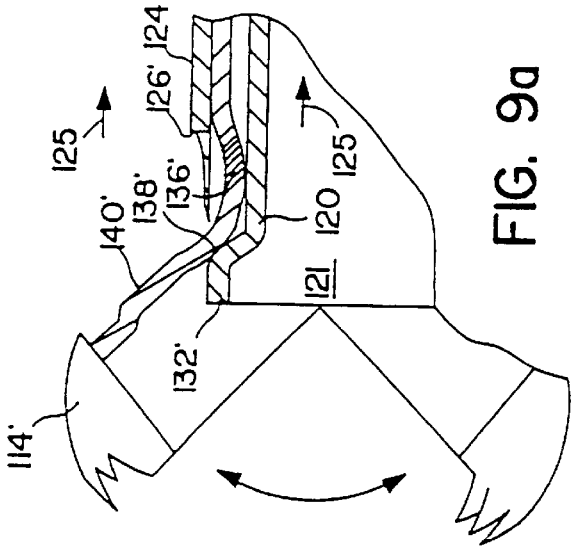
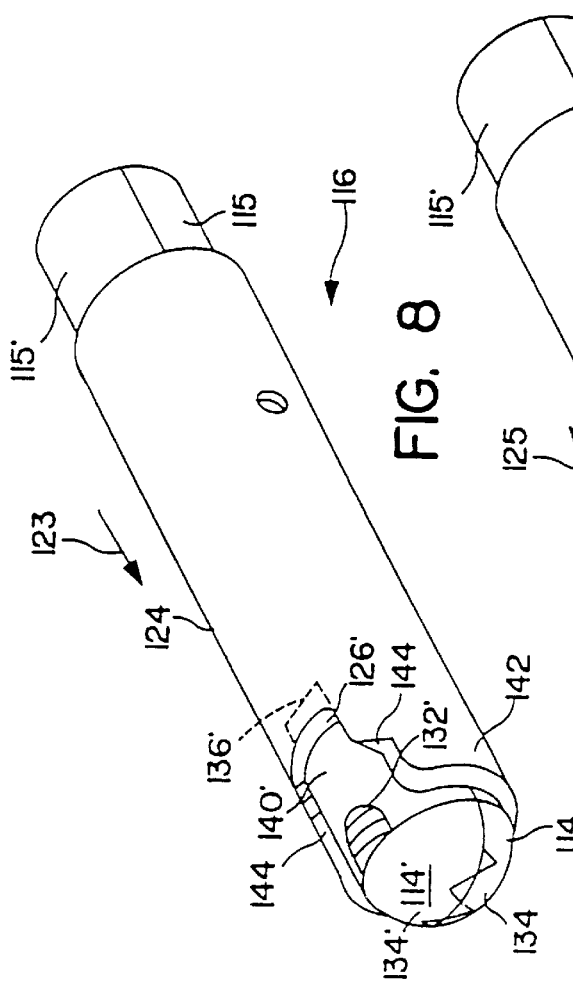
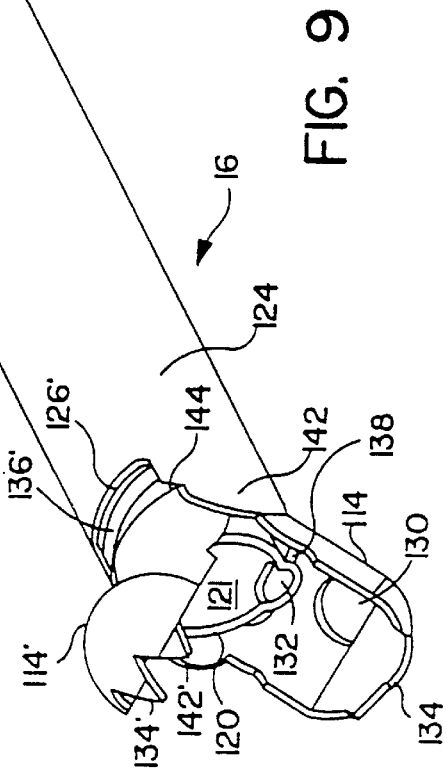

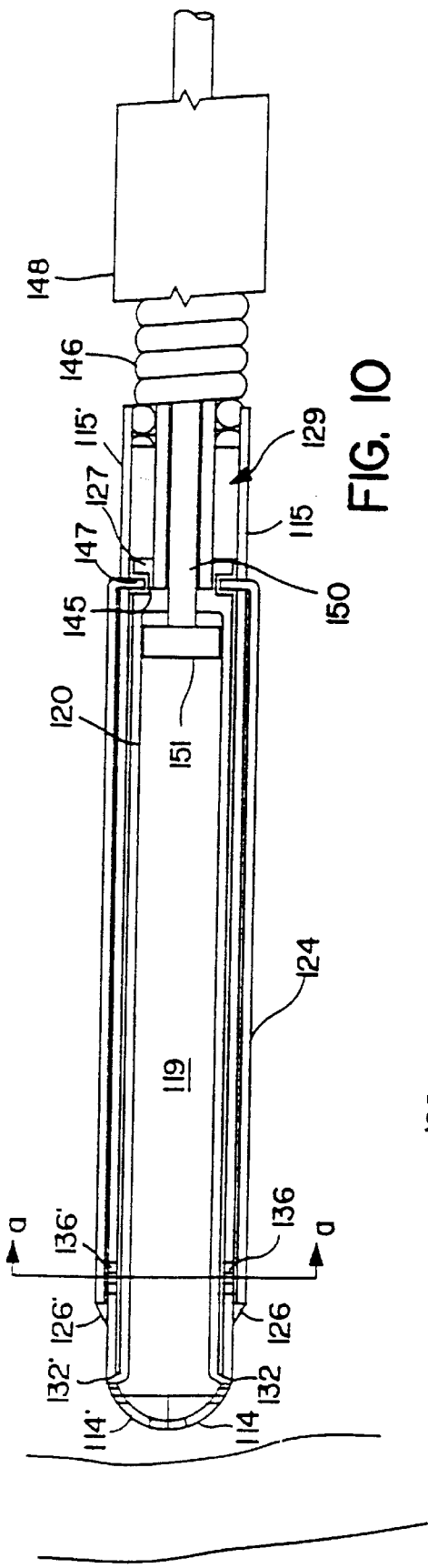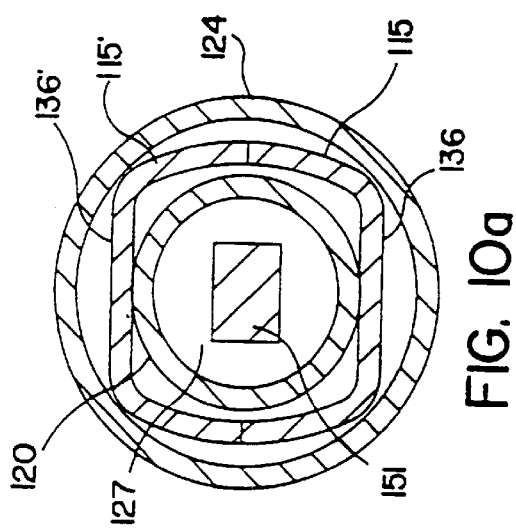
FIG. 10
FIG. 10a

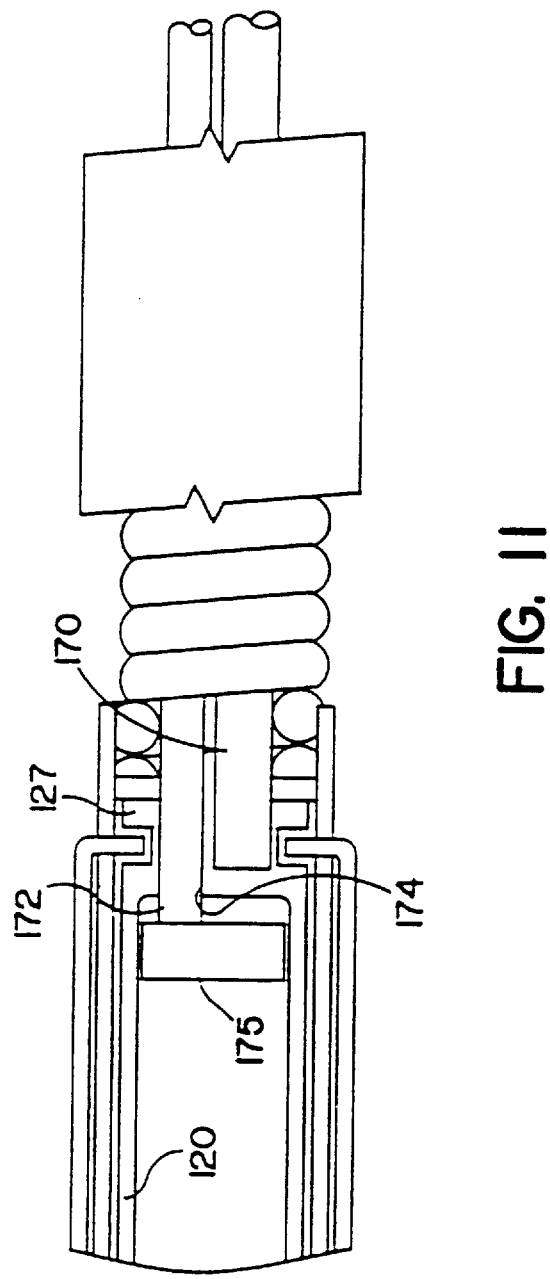

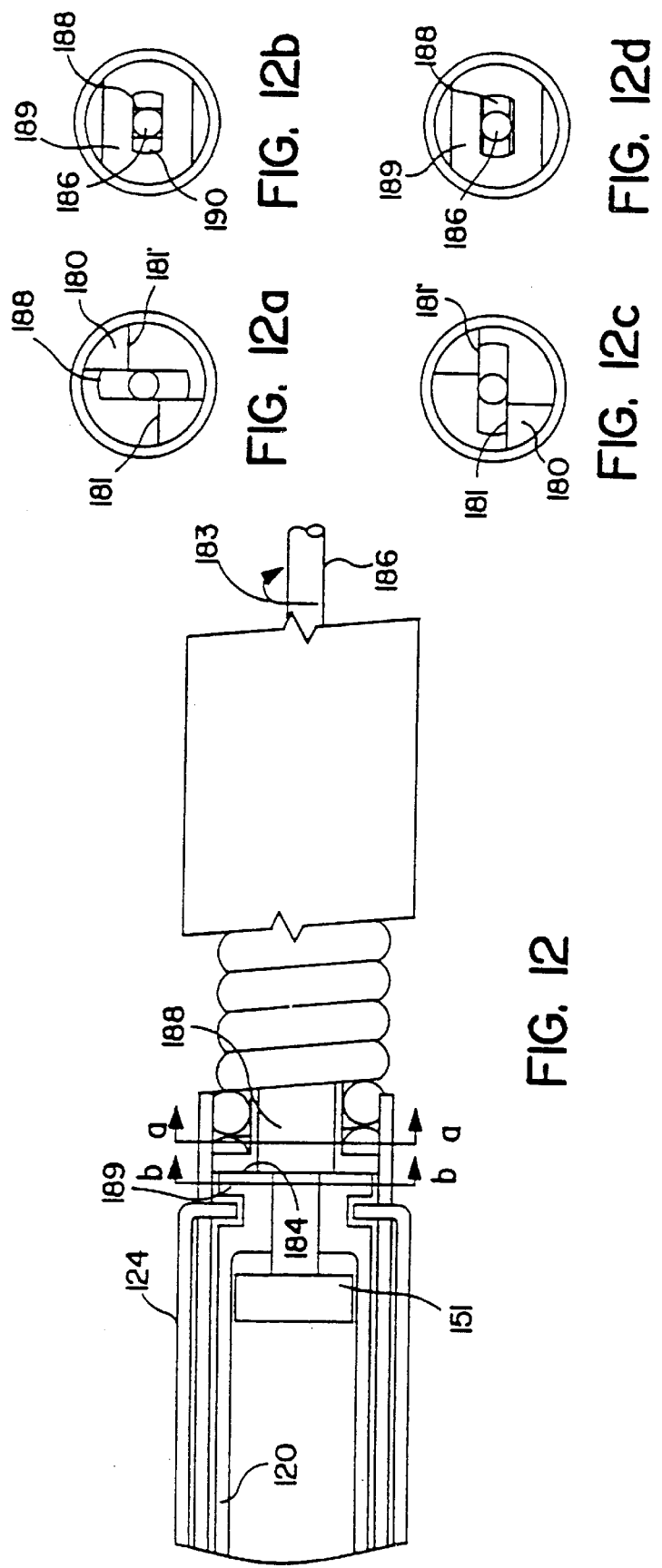

MOVEABLE SAMPLE TUBE MULTIPLE BIOPSY SAMPLING DEVICE

This is a continuation of application Ser. No. 08/193,382 filed on Feb. 8, 1994, now abandoned.

FIELD OF THE INVENTION

This invention relates to taking samples of tissue from the body.

BACKGROUND OF THE INVENTION

Tissue samples can be examined in a laboratory to determine the presence of a pathological disorder (e.g. malignancy). Often, the samples must be obtained from deep within the body using a medical sampling instrument that is introduced beneath the skin. It is usually best to obtain several samples around the location where the disorder is suspected so that the presence and progress of disease, if any, can be accurately determined. The samples must be catalogued according to the location from which each sample is taken and the integrity of the samples must be maintained for the subsequent laboratory analysis.

SUMMARY OF THE INVENTION

In one aspect, the invention relates to an instrument for obtaining tissue samples from a site deep within the body, having an elongated proximal portion that is constructed to follow a long, torturous path to the site and a distal end constructed to remove a tissue sample from the body, including tissue specimens, polyps or the like. The instrument includes a sampling assembly with a jaw-like cutting member, a plastically deformable hinge operatively connected to the cutting member, and a deforming-force control element. The assembly is constructed such that the cutting member can be actuated to be opened and closed to take tissue sample from the body by plastic deformation of the hinge caused by forces applied by the control element.

Embodiments may include one or more of the following features. The hinge is a biologically compatible, relatively inelastic metal component. The hinge is formed integrally with the cutting member. The hinge is formed integrally with the cutting member from an arc-form piece where the arc-form is modified at the hinge. The arc-form is modified at the hinge to form a substantially flat region. The thickness of the metal forming the hinge is less than the thickness of the metal forming the cutting member. The instrument constructed to take multiple biopsy samples without being withdrawn from the body by including storage space proximal of and adjacent the cutting member for storage of multiple, successively taken samples.

Embodiments may also include one or more of the following features. The cutting element is integral with the hinge and the control element is operatively connected to the cutting member such that forces applied by the control element to the cutting member cause plastic deformation of the hinge. The control element includes a bearing member that applies the force by bearing upon the cutting member. The control element includes inner and outer bearing members. The inner bearing member is constructed to apply radially outward, cutting element-opening forces from within the cutting member and the outer bearing member is constructed to apply radially inward, cutting element-closing forces by bearing on exterior portions of the cutting member. The inner bearing member and inner surfaces of the cutting member are cooperatively constructed and relatively axially moveable between a bearing location where the inner bearing member bears on the inner surfaces of the cutting member to apply the radially outward cutting element-opening force and a non-bearing location where the inner bearing member does not resist closing of the cutting element. The outer bearing member is a sleeve-form and the sleeve-form and cutting element are relatively moveable axially between a bearing location where the sleeve-form bears on exterior portions of the cutting member to apply the radially inward, cutting element-closing force and a non-bearing location where the sleeve-form does not resist opening of the cutting element. The inner and outer bearing members move axially together and are constructed such that when one of the bearing members is in a bearing location, the other bearing member is in a non-bearing location.

Embodiments may also include one or more of the following features. The instrument is constructed to take multiple biopsy samples without being withdrawn from the body by including storage space proximal of and adjacent the cutting member for storage of multiple, successively taken samples, by providing the inner bearing member on a hollow tube-form member having an opening capable of receiving samples cut by the cutting member and an elongated storage area proximal thereof for storing the multiple, successively taken samples. The tubular element is constructed to move axially distally as the cutting member is closed during taking of a sample to assist in urging the sample into the opening.

In another aspect, the invention relates to an instrument for obtaining tissue samples from a site deep within the body. The instrument has an elongated proximal portion that is constructed to follow a long, torturous path to the site and has a distal end constructed to remove a tissue sample from the body, including tissue specimens, polyps or the like. The instrument is constructed to take multiple biopsy samples from the body. The instrument includes a cutting and storage assembly having a jaw-like cutting member that can be actuated to be opened and closed to take the sample. The assembly has an inner, hollow tube-form member with an opening to receive samples and an elongated storage area proximal thereof for storing multiple, successively taken samples. The inner hollow member is constructed to move distally relative to the cutting member during closing of the cutting member to assist in urging the sample into the opening and in displacing previously taken samples axially proximally.

Embodiments may include any of the features already mentioned, and in particular one or more of the following features. The assembly is constructed of inner, middle, and outer concentrically arranged tube-form members. The middle member includes at its distal end the jaw-like cutting member and a hinge region operably connected to the cutting member such that the cutting member can be opened and closed to take the sample from the body. The inner and outer concentric members are axially moveable together relative to the middle member to effect opening and closing the cutting member such that proximal relative motion causes the inner member to create a radially outward opening force and distal motion causes the outer member to create a radially inward closing force. The inner member includes at its distal end a radial protrusion that bears on cooperatively formed surfaces on the cutting member to open the cutting member. The cutting member includes a slot opening positioned to align with the protrusion when the cutting member is closed, so the protrusion does not resist the closing force caused by the outer member. The outer member includes a bearing surface offset proximally from the protrusion so the outer member does not resist the opening force applied by the inner member. The hinge region is formed of a biologically compatible metal and operates by plastic deformation. The hinge is formed by modifying an arc-form profile of the tubular member to include a substantially flat region. The outer member further includes guiding surfaces, extending axially adjacent the cutting member to guide the opening and closing movement of the cutting member. The instrument includes multiple cutting members that can be cooperatively actuated to be opened and closed to take the sample.

In another aspect the invention features an instrument for grasping items or tissue in connection with a medical procedure. The instrument includes a sampling assembly with a jaw-like member that can be radially actuated to be opened and closed to take tissue sample from the body. The instrument includes inner and outer control elements constructed such that the inner control element contacts inner surfaces of the jaw-like member to assist in opening and the outer control element contacts outer surfaces of the jaw-like members to assist in closing.

Embodiments may include one or more of the following features. The jaw-like cutting member is radially actuated by bending a plastically deformable hinge. The control elements are constructed to bear on the jaw-like member to cause the bending.

In another aspect the invention features an instrument for grasping items or tissue in connection with a medical procedure. The instrument includes a sampling assembly with a jaw-like member formed integrally on a tube-form, a co-extensive control member that can be actuated to radially open and close the jaw to take tissue sample from the body, and a jaw-guiding element constructed to resist side loading applied to the jaw.

Embodiments may include one or more of the following features. The jaw-guiding element is a proximal extension attached to the jaw that can bear on the control element to resist the side loading. The device includes inner and outer tube-form control elements. The inner control element is constructed to contact inner surfaces of the jaw-like member to assist in the opening. The outer control element is constructed to contact outer surfaces of the jaw-like members to assist in the closing. The jaw guiding element extends into space between the inner and outer control elements. The jaw-guiding element has a degree of elasticity that prevents plastic deformation under typical side loads. The control element extends concentrically over the tube-form and the jaw-guiding element includes distal extensions adjacent the jaw-like members.

Other features and advantages follow.

BRIEF DESCRIPTION OF THE DRAWINGS

We first briefly describe the drawings.

FIG. 2 is an enlarged perspective view, and FIG. 2a is a cross-sectional view of the jaw area, of an embodiment of the invention with the jaws open;

FIGS. 3 and 3a are similar perspective and cross-sectional views, respectively, of the embodiment but with the jaws closed;

FIG. 4 is a cross-sectional side view of the embodiment including views of the coupling to proximal portions of the device and FIGS. 4a–4c are end-on cross-section taken across lines indicated in FIG. 4;

FIGS. 5–5f illustrate a use of the embodiment;

FIG. 7 is a perspective view of a sample tube;

FIG. 8 is an enlarged perspective view and FIG. 8a is a cross-sectional view of the jaw area of another embodiment of the invention with the jaws open;

FIGS. 9 and 9a are similar perspective and cross-sectional views, respectively, of the embodiment of FIGS. 8 and 8a but with the jaws closed;

FIG. 10 is a cross-sectional side view of the embodiment of FIGS. 8 et seq. including the coupling to proximal portions of the device and FIG. 10a is an end-on cross-sectional view taken along the hinge, lines aa in FIG. 10;

FIG. 11 is a cross-sectional view of the coupling portions of an alternative embodiment of the invention;

FIGS. 12–12d are cross-sectional views of the coupling portions of an alternative embodiment of the invention.

DESCRIPTION OF THE PREFERRED EMBODIMENTS

General Description

Figure 1:
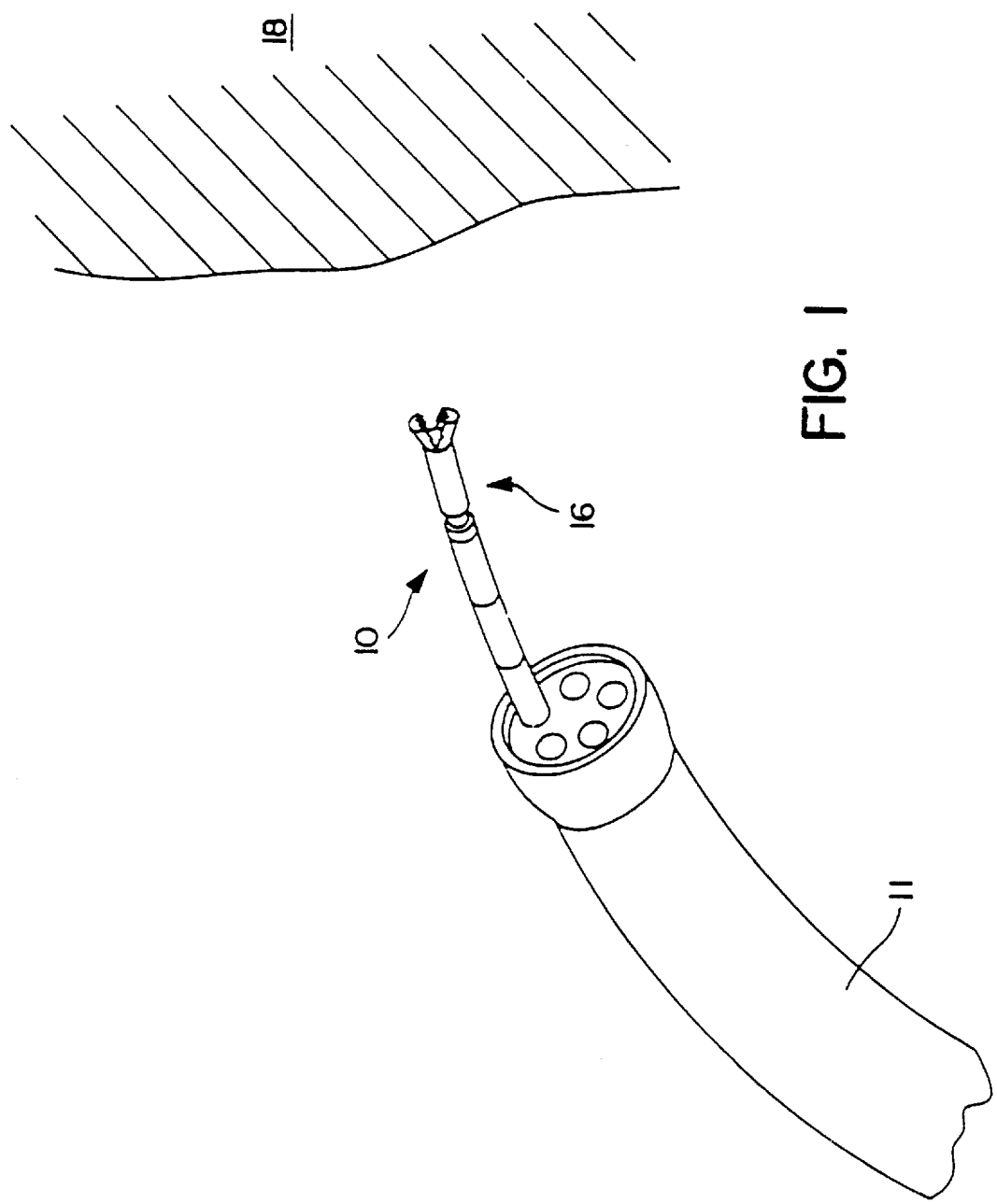
FIG. 1 is a perspective view of an embodiment of the invention being delivered into the body through an endoscope.

Referring to FIG. 1, the device 10 for multiple biopsy sampling may be delivered into the body through the channel of an endoscope device 11 (e.g., gastroscope, sigmoidoscope, or colonoscope). The endoscope device typically has a length of about 100–250 cm and a channel diameter of 2.0–3.8 mm, typically about 2.8 mm. A distal sampling portion 16 is extended from the endoscope for cutting and storing a sample of tissue from a body surface 18 of a patient (e.g. from a surface in the gastrointestinal tract or bronchial tract). The device has a diameter of preferably around 1.8–2.4 mm, typically about 2.3 mm or less and is of sufficient flexibility so it passes easily though the channel when the endoscope follows a tortuous body passageway. The endoscope includes other lumens for water, air, suction, and viewing. Devices according to the invention can be adapted to be introduced to sites (e.g., urinary tract, reproductive organs, cardiac tissue, or the like) deep within the body by other means. For example, a device can be configured with a lumen so that it can be advanced over a guidewire, e.g., in vascular applications. The device may be passed through an introducer or guiding catheter in, e.g., cardiac applications. The sampling and storage arrangements may be useful in open surgery applications.

Referring particularly to FIGS. 2–3a, the sampling portion 16 includes a pair of jaws 14, 14' that can be radially opened and closed by bending plastically deformable hinges 36, 36'. The device also includes an inner, axially moveable sample tube 20 with jaw-opening bumps 32, 32' and an outer, axially moveable jaw-closing sleeve 24 with bearing portions 26, 26'. The sample tube 20 and outer sleeve 24 move together to open and close the jaws 14, 14' by applying camming forces to the jaws that plastically deform the hinges 36, 36'. Referring particularly to FIGS. 2 and 2a, with the sample tube 20 and outer sleeve 24 retracted relative to the jaws (arrows 23), the bumps 32, 32' bear on inner bearing surfaces 38, 38' forcing the jaws into an open position by bending the hinges 36, 36'. Referring particularly to FIGS. 3–3a, with the sample tube 20 and outer sleeve 24 extended relative to the jaws (arrows 25), the bearing portions 26, 26' of the outer sleeve bear on outer bearing surfaces 43, 43' forcing the jaws into a closed position. The sample tube 20 defines a sample storage space 19 where previous samples can be stored while succeeding samples are taken, thus allowing multiple samples to be taken without removing the device from the endoscope. Moreover, the axial motion of the sample tube in the distal direction during jaw closure helps urge the tissue sample that is being cut into the open end 21 of the tube.

The jaws 14, 14' are formed integrally at the end of two elongated stainless steel tube-forms 15, 15'. The hinges 36, 36' are formed by flattening a section of the tube-forms at a location just proximal of the jaws. Flattening the hinges reduces stress build-up and improves low-cycle fatigue life, allowing more open-close cycles. As illustrated, the length of the generally rectangular hinges define rotational axes about which the jaws are radially opened and closed. An advantage of the plastically deformable hinge is that it can be formed of common, inexpensive and relatively inelastic, biocompatible metals, such as stainless steel, without providing a complex spring-bias or pivoting arrangement. The jaws can be formed integrally with the hinge and their radial motion can be controlled accurately and easily over the entire opening and closing range.

The jaws include ends 34, 34' with edges suitable to scrape and cut samples of tissue from a body surface. The ends of the jaws have a shallow interior curvature so the open end 21 of the sample tube can be positioned close to the inner surface of the ends of the jaws to help urge a sample into the tube. The jaws also include slots 30, 30' through which the bumps 32, 32' on the sample tube may extend so the bumps do not interfere with the jaws when they are closing. The jaws are formed with ear-forms 40, 40' that extend proximally into the clearance between the outer sleeve 24 and sample tube 20. The ear-forms can bear on the outer surface of the sample tube and inner surface of the sleeve to resist side loads applied to the jaws to keep the jaws in alignment. The ear-forms, because of their thinness and length, have a degree of elasticity. They are not plastically deformed by reasonable side loads but instead spring back to properly align the jaws after release of a side load. During radial motion of the jaws, the ear-forms are guided by pins 42, which extend from the outer wall of the sample tube. The pins 42 are also fixed to the sleeve so that the sleeve and sample tube move axially together. (As will be discussed further below, the sample tube and sleeve may be joined at other points as well.) The jaws are prevented from opening beyond a desired width by a surface 44 on the ear-forms that is complementary with the circumference of the pins and acts as a stop. The bearing portions 26, 26' also bear against the jaws when they are in the fully open position, which helps support the jaws by resisting axial forces that could otherwise tend to force them open beyond the desired width. The sleeve includes axial slits 80 so that the end of the sleeve flexes slightly outward (FIG. 2a) which helps the jaws resist excessive axial distal forces and helps apply the camming force to the jaws when the sleeve is extended distally during jaw closure.

Referring to FIG. 4, the sampling portion 16 can be actuated from the proximal end of the device, outside the body, by using an axially moveable jaw actuation wire 52 that is fixed to the proximal portion of the sample tube 20. As mentioned, the sample tube 20 and outer sleeve 24 are coupled. Thus, they move axially together under control of the actuation wire 52. The axial position of the jaws relative to the sample tube and sleeve is maintained by tension wires 55, 55', which are attached to the proximal portion of tube-forms 15, 15'. A sample discharge wire 56 extends into the sample space 19 to a discharge head 54. The discharge wire 56 can be actuated distally to push samples out of the sample tube with the head after the device is removed from the body.

A flexible polymer sheath 48 (FIG. 2) is attached to the distal end of the jaw tube-forms and extends proximally covering the tension wires, actuation wire, and discharge wire. The sheath may be provided with separate lumens for each wire. The tension wires can also be embedded in the wall of the polymer sheath. The axially-extending tension wires substantially carry the tension load needed to hold the jaw tube-forms axially stationary as the sample tube and outer sleeve move during actuation of the jaws. This provides a strong yet flexible device that can be easily threaded through a tortuous passageway, while eliminating the need for a thick, high tensile strength polymer sheath or a metal reinforcing coil. (Although in embodiments, those elements can be used if desired.)

Use

Referring to FIGS. 5–5f, in use, the jaws 14, 14' of the device are first brought close to a tissue surface 18 where a sample, such as a mucosal sample, is to be taken. Referring particularly to FIG. 5a, the sleeve 24 and sample tube 20 are retracted together (arrows 23) to force open the jaw members 14, 14' by the camming action of the bumps 32, 32' on the inner bearing surfaces 38, 38' of the jaws. The sleeve 24, as it moves proximally, positions bearing portions 26, 26' so as not to interfere with the jaws or hinges during opening. With the jaws open, the device is advanced so the jaws are in contact with the tissue surface 18 (arrow 27). The ear-form features 44, in cooperation with the pins 42, and the bearing portions 26, 26', resting on the outer bearing surfaces 43, 43' of the jaws, prevent the jaw members from opening further if the device is urged axially against the tissue surface.

Referring to FIG. 5b, the sleeve 24 and sample tube 20 are then advanced distally (arrows 25). The bearing surfaces 26, 26' of the sleeve 24 bear on the outer surfaces 43, 43' of the jaws, forcing them to close and scrape and cut sample from the tissue surface. The bumps 32, 32' on the sample tube align with and extend through the openings 30, 30' on the jaws so as not to interfere with jaw closure. As the jaws close in radial motion, they urge tissue separated from the surface slightly proximally. At the same time, the sample tube 20 moves axially distally. The combined effects of the jaws and the tube tend to urge or stuff the sample into the open end 21 of the sample tube 20.

Referring to FIG. 5c, when the sleeve and the sample tube are pushed to their full distal positions, the jaw members are completely closed and the first sample 60 is separated from the tissue surface and collected in the sample tube 20.

Referring to FIG. 5d, subsequent samples 61–65 can be taken without removing the device from the endoscope by repeating the sequence above. The samples are stuffed into the sample tube in the order in which they were collected. The stuffing action helps displace previously taken samples proximally within the tube as a subsequent sample is taken. Further, the previously taken samples only move relative to the sample tube when a subsequent sample is urged into the tube. This feature has the advantage that the samples are not rubbed back and forth against the walls of the tube as the tube moves axially.

Referring to FIGS. 5e and 5f, to discharge the samples 60–65 once the device has been removed from the endoscope, sleeve 24 and sample tube 20 are retracted to open the jaw members (arrow 23). Referring particularly to FIG. 5f, the sample discharge wire 56 is then advanced distally so that the discharge head 54 engages sample 60 and pushes the samples out of the tube and into a collection container.

Detailed Description

The following is a more detailed description of the embodiment described above. Refer particularly to FIGS. 4–4c, which show components in cross sectional views with the device assembled and to FIGS. 6–7, which show views of a jaw tube-form and the sample tube before assembly.

Figure 6:
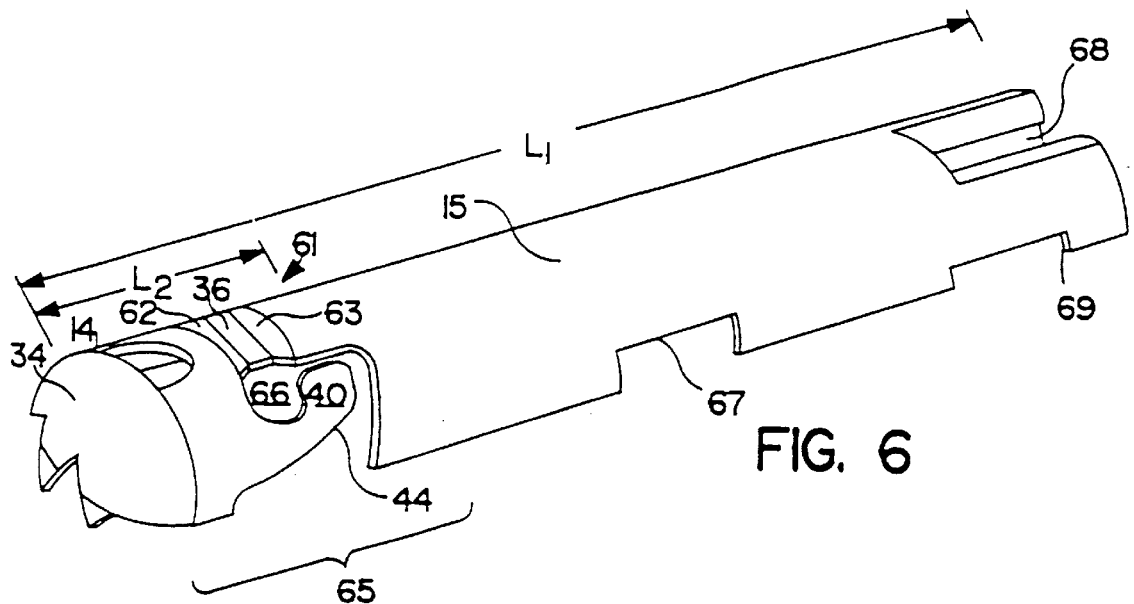
FIG. 6 is a perspective view of a jaw tube-halve.
Figure 6A:
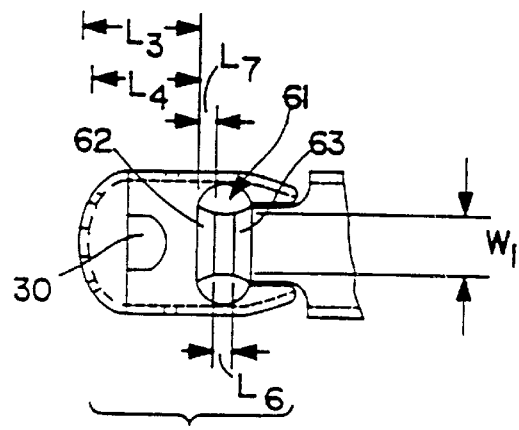
FIG. 6a is a top view and FIG. 6b is a side view of the jaw and hinge area.
Figure 6B:
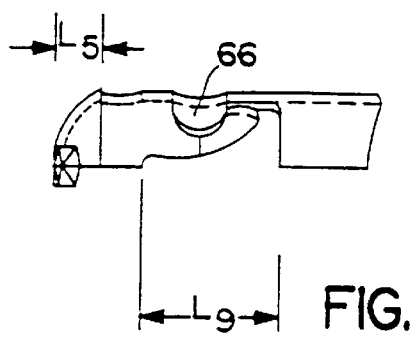

Referring particularly to FIGS. 6–6b, the jaw tube-form 15 is made of stainless steel (e.g. 301, 302 or 304 ss). (The other jaw tube-form 15' is constructed similarly.) The tube-form has an overall length $L_1$, about 0.367 inch. The jaw and hinge portion 65 has a length, $L_2$, about 0.100 inch. The wall thickness of the tube-form is about 0.005 inch. The tubular portions define an arc with outer diameter of about 0.081 inch. The hinge is recessed from the outer diameter of the tube by about 0.0015 inch, has length $L_6$, about 0.01 inch, and a width W1, about 0.03 inch. The hinge region 61 also includes short ($L_7$, about 0.01 inch), transition regions 62, 63, which are formed in the stamping process. As illustrated, portions of the tube circumferentially adjacent the hinge area are removed to form generally circular cut-outs 66 with a radius of about 0.012 inch. The cut-outs help the smooth operation of the hinge by decoupling portions of the tube-forms that are not on the bending axis. The cut-outs also help smooth operation by reducing the frictional contact of the jaw ear-forms 40, 40' with the sample tube and the sheath when there is no side loading on the jaws. The ear-forms are integral with the jaws, thus having the same thickness, and extend a distance $L_9$, about 0.071 inch, (FIG. 6b).

The jaws extend a length $L_4$, about 0.068 inch, beyond the hinge region (FIG. 6a). The opening 30 in the top of the jaw, through which the bump 32 on the sample tube passes when the jaw is being closed, is roughly semicircular with a radius of about 0.016 inch (FIG. 6a). The blunt end of the jaw defines a radius of about 0.044 inch and extends axially a distance $L_5$, about 0.027 inch (FIG. 6b). The inner surface of the jaws defines a radius of about 0.039 inch. In this embodiment, the open end of the sample tube can be located about 0.025 inch from the inner surface of the ends of the jaws.

As mentioned, the jaw ear-forms are shaped to travel along pin 42 during jaw motion and to provide a stop that prevents the jaws from opening beyond a desired point. In this embodiment, the jaws can open to a half-angle of about 45°. The end 34 of the jaw is provided with teeth that extend about 0.012 inch and may be sharpened to aid in cutting tissue. The proximal portions of the tube-form include a key and slot 67 arrangement to resist shear forces and maintain the relative axial position of the two tube-forms after they have been assembled and attached, e.g by spot welding. (A key on the other tube half is not shown; nor is the key on the other side of tube-form 15 visible.) A slot 69 is provided for a pin 71 that extends between the sample tube and the sleeve (see FIGS. 4b and 7). The slot 69 has a length of about 0.058 inch, which corresponds approximately to the maximum stroke of the sleeve and sample tube during actuation of the jaws. The proximal end of the tube-form includes a bent-in feature 68, sized with length of about 0.065 inch and radius of about 0.008 inch, that accepts the distal portion of tension wire 55 which is fixed at the feature 68 by spot welding. The tension wire is made of stainless steel and has a diameter of about 0.016 inch. The tube-form 15 is longer than the sleeve 24 to provide a surface for attaching the polymer sheath 48, for example, with epoxy.

Referring to FIG. 7, sample tube 20, formed of stainless steel, has an overall length $L_8$ about 0.473 inch, a diameter of about 0.065 inch, and a wall thickness of about 0.004. The outer surface of the sample tube includes guide pin 42 and proximal pin 71, which can be formed by crimping the wall of the tube (e.g. FIG. 4b). Both pins are attached to the inner wall of the sleeve, e.g., by spot welding, so that the sleeve and sample tube move axially together (see FIG. 4b). (The jaw tube-forms are constructed to include axial slot 69 in which the pin 71 may travel as the sample tube moves axially when the jaws are actuated (see FIG. 6).) The distal end of the sample tube includes jaw opening bumps 32, 32' which extend radially about 0.009 inch from the outer surface of the tube. The bumps have the shape of a quarter-sphere, with a radius of about 0.015 inch, so that the jaws are opened gradually when the sample tube moves proximally. The distal end of the sample tube includes a bent-in feature 73 to which the control wire is attached by crimping and welding.

The sleeve, also stainless steel, has an overall length of about 0.344 inch, an inner diameter of about 0.085 inch and a wall thickness of about 0.005 inch. The clearance between the outer surface of the sample tube and the inner surface of the sleeve, in which the jaw ear-forms travel, is about 0.010. The sleeve includes at the proximal end slits 80, 80' (slit 80' not shown) that run axially from the distal end a distance of about 0.033 inch (FIG. 3). The slits allow the distal end of the sleeve to elastically bend outward slightly as the bearing portions are urged against the jaws during closure (FIG. 2a).

The actuation wire is made of stainless steel and has a diameter of about 0.024 inch. The sample discharge wire is also formed of stainless steel and has a diameter of about 0.021 inch. The discharge head has a diameter of about 0.051 inch and a thickness of about 0.015 inch.

Other Embodiments

Referring to FIGS. 8–9a, in another embodiment, sleeve 124 has jaw alignment guides 142, 142' that reduce the possibility of jaw bending because of side loadings on the jaws. Stop surfaces 144 limit the degree to which the jaws can be opened radially. The sleeve 124 is configured to properly locate bearing surfaces 126, 126' relative to the hinges 136, 136'. In the jaw-closed position, the bearing surfaces extend over or distally beyond the hinge but are proximal of the slots in the jaws so that the bumps on the sample tube can extend through the slots. As the sleeve is drawn proximally, during opening of the jaws, the bearing surfaces 126, 126' are positioned proximally of hinges 136, 136' so that they can be plastically deformed without interference from the sleeve 124.

Referring particularly to FIGS. 10–10a, the sample tube 120 and sleeve 124 are coupled at a coupling portion 127 (integral with the sample tube) to maintain their axial alignment as they advance and retract. The sleeve 124 includes radial extensions 147 that mate with slots 145 in the coupling portion. The sections of the sleeve adjacent to extensions 147 travel in axial openings (not shown) through tube-forms 115, 115' during axial motion of the sleeve.

The axial motion of the sample tube and sleeve relative to the jaws is controlled from the proximal end of the device. The coupling portion 127 couples to a control tube 129 (e.g. stainless steel hypotubing) which extends through a flexible coil jacket 146, encased in a polymer sheath 148 (e.g. teflon, polypropylene, or polyethylene), to the proximal end of the device outside the body. The control tube includes in its lumen a sample discharge push rod 150 with a pushing head 151 in the sample space 119. When taking samples, the push rod 150 travels with the control tube 129. (For example, they may be coupled at the proximal end.) To remove samples, after the jaws have been opened, the sample discharge push rod 150 is uncoupled from the control tube and moved distally to push the samples from the sample tube distally.

Referring to FIG. 11, in an alternative embodiment, two non-concentric wires are used to actuate the device. The device includes a jaw actuating wire 170 connected to the coupling portion 127 of sample tube 120 and a smaller sample discharge actuating wire 172 running through an opening 174 in the coupling portion 127 and connected to the proximal end of the sample discharge pushing head 175. During sample collection, while the jaw is being opened and closed, relative motion between sample discharge wire 172 and jaw actuation wire 170 is prevented by a mechanism at the handle. After all the samples have been obtained, the sample discharge actuating wire 172 is released by the handle mechanism so that it can advance relative to the jaw actuation wire to push the samples from the sample tube.

Referring to FIGS. 12–12b, in an alternative embodiment, a single wire 186 is used to open and close the jaws as well as to discharge the samples. Wire 186 is formed with a rectangular key 188 and the coupling portion 189 includes a rectangular opening 190. To advance or retract the sample tube and sleeve, the system is configured as shown in FIGS. 12–12a. The key 188 engages the proximal end 184 of sample tube 120 as the wire is advanced. The pushing head 151 engages the distal end of the coupling portion as the wire is retracted.

Referring particularly to FIGS. 12c and 12d, to remove the samples from the sample tube, the actuating wire 186 is rotated 90 degrees (arrow 183, FIG. 12) so the key portion 188 engages surfaces 181, 181' of stops 180. The key then lines up with opening 190 in the coupling portion so the key and the wire can then be advanced through the opening causing the sample discharge push rod to move relative to the sample tube discharging the samples.

In other embodiments, rather than, or in combination with flattening the tube, the hinges are formed by reducing the thickness of the metal at the hinge locations. The thickness may be reduced (e.g. by stamping), for example, to a thickness of about 0.003–0.004 inch. The reduced thickness makes the jaws easier to operate because less force is required to plastically deform the hinge. In addition, a thinner metal at the hinge reduces stress build-up. At the same time, the jaws themselves can be made of a thicker metal so they can be formed with sharp cutting edges and are strong and stiff enough to exert substantial radial force on the tissue surface without bending.

Different metals can be used in the hinges and jaws by forming them separately and then fastening them together, for example by braising, welding, or mechanical couplers. An advantage of the invention is that the device, especially the jaws and hinge, can be constructed from common biologically compatible metals such as stainless steel. These metals are often substantially inelastic but can be plastically deformed by reasonable force. However, in embodiments, a highly elastic metal might be used for the hinge and biased to help open or close the jaws. Relatively inelastic metals can also be used with spring loaded assists. In embodiments, the device may use stress induced or temperature induced superelastic materials. Titanium alloys can be used, e.g., at the hinges, especially in plastically deformable embodiments. The device also can be constructed such that the jaws are at rest in an intermediate open position. The jaws can then be fully opened or closed by actuating the sample tube and sleeve, as discussed, which plastically or elastically deforms the hinge. In other embodiments, the device is constructed so the jaws are moved axially, while the sample tube and sleeve remain stationary.

In embodiments, the sample tube can be removed from the device after several samples have been taken. For example, the tube can be releasably coupled to the coupling portion using a quarter turn slot configuration or a radial squeeze-release arrangement. A new sample tube can be inserted into the device to take additional samples from the patient. The sample tubes can be removed either by extending them distally through the open jaws or by an arrangement that permits the tubes to be withdrawn proximally while the rest of the device remains inside the body. Such an arrangement would use a mechanical decoupling assembly to decouple the sample tube from the sheath and a geometry that allows the bearing bumps at the distal end of the tube to be withdrawn proximally through the entire length of the device. After removing the tissue, the sample tube can be clipped to a holder bearing patient identification and other pertinent information.

In embodiments, the samples may be removed by the force of fluid pressure in the distal direction. For example, holes could be provided near the proximal end of the sample tube through which a fluid is pumped behind the samples to push them out of the tube. Alternatively, a syringe may be positioned over the distal end of the tube and the samples drawn out of the tube by vacuum.

In embodiments, the sample tube may also include a structure that acts to retain and/or separate the samples. For example, the tube may be constructed of a semi-rigid polymeric material with internal texture, such as ribbing or other topographical features that retain the samples. Slots, holes or other forms of permeable walls can be provided so that fixing and embedding solutions can be passed into the tube.

In still further embodiments, the jaws, sample tube and sleeve are all removable and disposable after samples have been taken; the proximal portions of the device, including the coupling portion, can then be reused by attaching a new assembly.

A system for taking multiple biopsy samples is taught in Chu "Instruments for Collecting Multiple Biopsy Specimens", U.S. Ser. No. 062,671, filed May 17, 1993, the entire contents of which is hereby incorporated by reference. Another system is taught in U.S. Ser. No. 08/124,272, filed Sep. 20, 1993, which is also incorporated herein by reference. Another system is taught in U.S. Ser. No. 08/129,653, filed Sep. 30, 1993, which is also incorporated herein by reference. Another system is taught in U.S. Ser. No. 08/146,447, filed Oct. 29, 1993, which is also incorporated herein by reference. Another system is taught in "Multi-Motion Side-Cutting Multiple Biopsy Sampling Device" by Banik and Robinson, and filed the same day as this application which is also incorporated herein by reference. Another system is taught in "Multi-Motion Cutter Multiple Biopsy Sampling Device", by Banik and Robinson, and Still other embodiments are within the following claims. For example, the device, e.g., the jaws, the hinge, the sleeve and the sample tube, may be constructed of plastic and/or have variations from the dimensions taught here.

What is claimed is:

1. An instrument for obtaining tissue samples from a site within the body, the instrument having a flexible elongated proximal portion for following a path to said site, and having a distal end for removing a tissue sample from the body, wherein said instrument includes a sampling assembly having a jaw-type cutting member having an outer surface and an inner surface, a deformable hinge operatively connected to said cutting member, an inner control member disposed radially inward of said cutting member, and a movable outer control member positionable radially outward of said cutting member, said inner and outer control members adapted to open and close the cutting member to obtain said tissue sample from the body.

2. The instrument of claim 1 wherein said hinge is a biologically compatible, relatively inelastic metal component.

3. The instrument of claim 2 wherein said hinge is formed integrally with said cutting member.

4. The instrument of claim 2 or 3 wherein said hinge is formed integrally with said cutting member from an arc-form piece where a shape of said arc-form is modified at said hinge.

5. The instrument of claim 4 wherein said arc-form is modified at said hinge to form a substantially flat region.

6. The instrument of claim 3 wherein the hinge and cutting member are formed of metal and the metal is thinner at said hinge than at portions of said cutting member adjacent said hinge.

7. The instrument of any one of claims 1, 2 or 3 including storage space proximal of and adjacent said cutting member for taking and storage of multiple samples without withdrawing said device from the body.

8. The instrument of claim 1 wherein said outer control member is an outer bearing member that applies said force by bearing on said outer surface of said cutting member.

9. The instrument of claim 8 wherein said inner control member comprises an inner bearing member that applies said force by bearing upon said inner surface of said cutting member.

10. The instrument of claim 9 wherein said inner bearing member applies radially outward, cutting element-opening forces from within said cutting member and said outer bearing member applies radially inward, cutting element-closing forces.

11. The instrument of claim 9 wherein said inner bearing member and inner surface of said cutting member are cooperatively constructed and relatively axially moveable between a bearing location where said inner bearing member bears on said inner surface of said cutting member to apply said radially outward cutting element-opening force and a non-bearing location where said inner bearing member does not interfere with closing of said cutting element.

12. The instrument of claim 11 wherein outer bearing member comprises a sleeve-form and said sleeve-form and said cutting element are relatively moveable axially between a bearing location where said sleeve-form bears on exterior portions of said cutting member to apply said radially inward, cutting element-closing force and a non-bearing location where said sleeve-form does not interfere with opening of said cutting element.

13. The instrument of claim 12 wherein said inner and outer bearing members move axially together and are constructed such that when one of said bearing members is in a bearing location, the other bearing member is in a non-bearing location.

14. The instrument of claim 10 wherein said inner bearing member is provided on a hollow tube-form member having an opening capable of receiving samples cut by said cutting member and an elongated storage area proximal thereof for storing said multiple, successively taken samples.

15. The instrument of claim 14 wherein said tubular element is constructed to move axially distally as said cutting member is closed during taking of a sample to assist in urging said sample into said opening.

16. An instrument for obtaining multiple tissue samples from sites within a body, the instrument having a flexible elongated proximal portion for following a path to said sites, and having a distal end for removing a tissue sample from the body, said instrument comprising a cutting and storage assembly having a jaw-type cutting member that can be actuated to be opened and closed to take a tissue sample and an inner hollow tube-form member within said cutting member and having an opening to receive said sample and an elongated storage area proximal thereof for storing multiple samples, said inner hollow tube-form member and said cutting member being coupled such that during closing of said cutting member, said hollow tube-form member moves distally relative to the cutting member.

17. The instrument of claim 16 wherein said assembly is comprised of inner, middle, and outer concentrically arranged tube-form members, said middle member including at its distal end said jaw-type cutting member and a hinge region operably connected to said cutting member such that said cutting member can be opened and closed to take said sample from the body, and said inner and outer concentric members being axially moveable together relative to said middle member to effect opening and closing said cutting member such that proximal relative motion causes said inner member to create a radially outward opening force and distal relative motion causes said outer member to create a radially inward closing force.

18. The instrument of claim 17 wherein said inner member includes at its distal end a radial protrusion that bears on cooperatively formed surfaces on the interior surface of said cutting member to open said cutting member and said cutting member includes a slot opening positioned to align with said protrusion when said cutting member is closed, so said protrusion does not interfere with the closing force caused by said outer member.

19. The instrument of claim 18 wherein said outer member includes a bearing surface offset proximally from said protrusion so said outer member does not interfere with the opening force applied by said inner member.

20. The instrument of claim 17 wherein said hinge region is formed of a biologically compatible metal and operates by plastic deformation.

21. The instrument of claim 17 wherein said hinge is formed by modifying an arc-form profile of said tubular member to include a substantially flat region.

22. The instrument of claim 16 wherein said outer member further includes guiding surfaces, extending axially adjacent said cutting member to guide the opening and closing movement of said cutting member.

23. The instrument of claim 16 including multiple cutting members that can be cooperatively actuated to be opened and closed to take said sample.

24. An instrument for obtaining a tissue sample in connection with a medical procedure comprising:

a sampling assembly having a jaw-type member with an inner surface and an outer surface, said jaw-type member being actuatable to be opened and closed to take said tissue sample from the body, and an inner control member disposed radially inward of said jaw-type member and a movable outer control member positionable radially outward of said jaw-type member, wherein said inner control member contacts said inner surface of said jaw-type member to assist in said opening and said outer control member contacts said outer surface of said jaw-type member to assist in said closing.

25. The instrument of claim 24 wherein said jaw-type cutting member is radially actuated by bending a plastically deformable hinge, said control elements being constructed to bear on said jaw-type member to cause said bending.

26. An instrument for grasping items or tissue in connection with a medical procedure, comprising:
 a sampling assembly having a jaw-type member, and a deformable hinge connected to said jaw-type member, said jaw-type member being actuatable to radially open and close to obtain tissue sample from the body by deformation of said hinge, and
 a jaw-guiding element associated with said jaw-type member and located proximal of said deformable hinge, said jaw-guiding element being positioned to resist side loading applied to said jaw-type member such that under an applied side load, said jaw type member can bear on a surface of said instrument to which said jaw type member is not directly connected.

27. The instrument of claim 26 wherein said jaw-guiding element comprises a proximal extension of said jaw-type member that can bear on a portion of said instrument proximal of said jaw-type member to resist said side loading.

28. The instrument of claim 27 wherein said jaw-type member includes an outer surface and an inner surface and said sampling assembly includes inner and outer tube-form control elements where said inner control element contacts said inner surface of said jaw-type member to assist in said opening and said outer control element contacts said outer surface of said jaw-type member to assist in said closing and,
 said jaw guiding element extends into space between said inner and outer control elements.

29. The instrument of claim 28 wherein said jaw-guiding element has a degree of elasticity that prevents plastic deformation under typical side loads.

30. The instrument of claim 26 further comprising a sleeve-form outer member, said sleeve form outer member and said jaw-type member being relatively moveable axially between a bearing location where said sleeve-form outer member bears on exterior portions of said jaw-type member to apply a radially inward, jaw-type member closing force and a non-bearing location where said sleeve-form outer member does not interfere with opening of said jaw-type member.

31. An instrument for grasping items or tissue in connection with a medical procedure, comprising:
 a sampling assembly having a jaw-type cutting member, and a deformable hinge connected to said cutting member, said cutting member being actuatable to radially open and close to take a tissue sample from a body by deformation of said hinge, and
 a movable outer control member positioned radially outward from said sampling assembly and positionable for applying a force to an outer surface of said cutting member such that said cutting member can be actuated to be closed to take the tissue sample from the body, said outer control member including a sleeve defining a distal end, the sleeve having a slit at the distal end to permit the distal end to flex outwardly.

32. The instrument of claim 31 wherein said sleeve and said jaw-type member are relatively moveable axially between a bearing location where said sleeve bears on exterior portions of said jaw-type member to apply said closing force and a non-bearing location where said sleeve does not interfere with opening of said jaw-type member.

33. An instrument for grasping items or tissue in connection with a medical procedure, comprising:
 a sampling assembly having a jaw-type member, and a deformable hinge connected to said jaw-type member, said jaw-type member being actuatable to radially open and close relative to a longitudinal axis of said instrument to take a tissue sample from a body by deformation of said hinge, and
 a jaw guide positioned to engage a guide element of said jaw-type member when said jaw-type member is fully open to resist axial loading applied to said jaw-type member which would tend to further open said jaw-type member, said guide element of said jaw-type member being located proximally of said deformable hinge.

34. The instrument of claim 33 wherein said guide element comprises a proximal extension of said jaw-type member, and said jaw guide comprises a pin along which said guide element rides during opening and closing of said jaw-type member.

35. The instrument of claim 34 wherein said jaw guiding element is exterior of said jaw-type member.

36. An instrument for grasping items or tissue in connection with a medical procedure, comprising:
 a sampling assembly having a jaw-type member, and a deformable hinge connected to said jaw-type member, said jaw-type member being actuatable to radially open and close to take tissue sample from the body by deformation of said hinge, and
 a jaw-guiding element associated with said jaw-type member, said jaw-guiding element including distal extensions that extend adjacent said jaw-type member from a portion of said device proximal of said jaw-type member to resist side loading applied to said jaw-type member such that under an applied side load, said jaw type member can bear on a surface of said instrument to which said jaw type member is not directly connected.

37. An instrument for grasping items or tissue in connection with a medical procedure comprising:
 a sampling assembly having a jaw-type cutting member with an inner surface and an outer surface, said jaw-type cutting member being radially actuatable to be opened and closed to take tissue sample from the body, and
 a movable inner control member and a movable outer control member, wherein said inner control member is positionable to apply a jaw-opening force to said inner surface of said jaw-type cutting member to assist in said opening and said outer control member is positionable to apply a jaw-closing force to said outer surface of said jaw-type cutting member to assist in said closing.

38. The instrument of claim 37 further comprising a deformable hinge operatively connected to said cutting member.

39. The instrument of claim 37 including storage space proximal of and adjacent said cutting member for taking and storage of multiple samples without withdrawing said device from the body.

* * * * *

UNITED STATES PATENT AND TRADEMARK OFFICE
CERTIFICATE OF CORRECTION

PATENT NO. : 5,871,453

DATED : February 16, 1999

INVENTOR(S) : Michael S. Banik et al.

It is certified that error appears in the above-indentified patent and that said Letters Patent is hereby corrected as shown below:

In Claim 8, Col. 11, line 34, change "is" to --comprises--;

In Claim 11, Col. 11, line 46, insert --said-- before "inner".

Signed and Sealed this

Twenty-fifth Day of May, 1999

Attest:

Attesting Officer

Q. TODD DICKINSON

Acting Commissioner of Patents and Trademarks